(12) United States Patent
Braithwaite

(10) Patent No.: US 7,207,330 B1
(45) Date of Patent: Apr. 24, 2007

(54) DELIVERY SYSTEM

(75) Inventor: Philip Braithwaite, Tewkesbury (GB)

(73) Assignee: Innovata Biomed Limited, St. Albans (GB)

( * ) Notice: Subject to any disclaimer, the term of this patent is extended or adjusted under 35 U.S.C. 154(b) by 2 days.

(21) Appl. No.: 09/980,999

(22) PCT Filed: Jun. 5, 2000

(86) PCT No.: PCT/GB00/02017

§ 371 (c)(1),
(2), (4) Date: May 20, 2002

(87) PCT Pub. No.: WO00/74754

PCT Pub. Date: Dec. 14, 2000

(30) Foreign Application Priority Data

Jun. 5, 1999 (GB) ............... 9913047.8
Jul. 13, 1999 (GB) ............... 9916283.6

(51) Int. Cl.
*A61M 15/00* (2006.01)

(52) U.S. Cl. ............... 128/203.15; 128/203.19

(58) Field of Classification Search ......... 128/200.14, 128/203.12, 203.15, 200.11, 200.17, 200.23, 128/200.24, 203.19, 203.21
See application file for complete search history.

(56) References Cited

U.S. PATENT DOCUMENTS

| | | | |
|---|---|---|---|
| 1,858,735 A | 5/1932 | Goodsell | |
| 2,587,215 A | 2/1952 | Priestly | |
| 3,008,609 A | 11/1961 | Sessions | |
| 3,439,823 A | 4/1969 | Morane | |
| 3,798,054 A | 3/1974 | Kawata et al. | |
| 3,854,626 A | 12/1974 | Krechmar | ......... 221/264 |
| 3,874,381 A | 4/1975 | Baum | |
| 3,876,269 A | 4/1975 | Fisher et al. | |
| 4,047,635 A | 9/1977 | Bennett, Jr. | |
| 4,114,615 A | 9/1978 | Wetterlin | |
| 4,174,034 A | 11/1979 | Hoo | ......... 206/1.5 |
| 4,200,099 A | 4/1980 | Guenzel et al. | |
| 4,274,403 A | 6/1981 | Struve | |
| 4,524,769 A | 6/1985 | Wetterlin | |
| 4,534,343 A | 8/1985 | Nowacki et al. | |
| 4,570,630 A | 2/1986 | Elliott et al. | |

(Continued)

FOREIGN PATENT DOCUMENTS

DE    14 98 398    1/1969

(Continued)

OTHER PUBLICATIONS

International Search Report of Aug. 28, 2000.

(Continued)

*Primary Examiner*—Teena Mitchell
(74) *Attorney, Agent, or Firm*—Nixon Peabody LLP

(57) ABSTRACT

There is described a medicament delivery device which comprises a medicament reservoir, a medicament delivery passage and a metering member adapted to transfer a measured dose of medicament from the medicament reservoir to the delivery passage characterized in that the device is provided with a moisture proof barrier. The medicament delivery device is especially suited for use as an inhaler. There is therefore also described an inhaler which provides improved airflow for the dispersion of medicament, and a method of treating patients suffering from a respiratory disorder.

6 Claims, 3 Drawing Sheets

U.S. PATENT DOCUMENTS

| | | | |
|---|---|---|---|
| 4,604,847 A | 8/1986 | Moulding, Jr. et al. | |
| 4,624,442 A | 11/1986 | Duffy et al. | |
| 4,627,432 A | 12/1986 | Newell et al. | |
| 4,635,829 A | 1/1987 | Brittingham, Jr. | |
| 4,668,218 A | 5/1987 | Virtanen | |
| 4,811,731 A | 3/1989 | Newell et al. | |
| 4,860,740 A | 8/1989 | Kirk et al. | |
| 4,882,210 A | 11/1989 | Romberg et al. | |
| 4,895,719 A | 1/1990 | Radhakrishnan et al. | |
| 4,907,583 A | 3/1990 | Wetterlin et al. | |
| 4,934,358 A | 6/1990 | Nilsson et al. | |
| 4,950,365 A | 8/1990 | Evans | |
| 5,002,048 A | 3/1991 | Makiej, Jr. | |
| 5,007,419 A | 4/1991 | Weinstein et al. | |
| 5,042,472 A | 8/1991 | Bunin | |
| 5,053,237 A | 10/1991 | Hendricks et al. | |
| 5,064,083 A | 11/1991 | Alexander et al. | |
| 5,067,491 A | 11/1991 | Taylor, II et al. | |
| 5,113,855 A * | 5/1992 | Newhouse | 128/203.12 |
| 5,152,422 A | 10/1992 | Springer | |
| 5,154,326 A | 10/1992 | Chang et al. | |
| 5,161,524 A * | 11/1992 | Evans | 128/203.15 |
| 5,169,029 A | 12/1992 | Behar et al. | |
| 5,192,528 A | 3/1993 | Radhakrishnan et al. | |
| 5,201,308 A * | 4/1993 | Newhouse | 128/203.15 |
| 5,207,217 A | 5/1993 | Cocozza et al. | |
| 5,208,226 A | 5/1993 | Palmer | |
| 5,253,782 A | 10/1993 | Gates et al. | |
| 5,263,475 A | 11/1993 | Altermatt et al. | |
| 5,295,479 A | 3/1994 | Lankinen | |
| 5,301,666 A | 4/1994 | Lerk et al. | |
| 5,320,714 A * | 6/1994 | Brendel | 128/203.15 |
| 5,347,999 A | 9/1994 | Poss et al. | 128/203.15 |
| 5,351,683 A | 10/1994 | Chiesi et al. | |
| 5,394,868 A * | 3/1995 | Ambrosio et al. | 128/203.15 |
| 5,409,132 A | 4/1995 | Kooijmans et al. | |
| 5,411,175 A | 5/1995 | Armstrong et al. | |
| 5,415,162 A | 5/1995 | Casper et al. | |
| 5,435,301 A | 7/1995 | Herold et al. | |
| 5,437,267 A | 8/1995 | Weinstein et al. | |
| 5,437,270 A * | 8/1995 | Braithwaite | 128/203.15 |
| 5,447,151 A | 9/1995 | Bruna et al. | |
| 5,450,160 A | 9/1995 | Tianello et al. | |
| 5,458,135 A | 10/1995 | Patton et al. | |
| 5,485,939 A | 1/1996 | Tucker | |
| 5,503,144 A | 4/1996 | Bacon | 128/203.15 |
| 5,520,166 A | 5/1996 | Ritson et al. | |
| 5,524,613 A | 6/1996 | Haber et al. | |
| 5,551,597 A | 9/1996 | Lambelet, Jr. et al. | |
| 5,562,231 A | 10/1996 | Lambelet, Jr. et al. | |
| 5,562,918 A | 10/1996 | Stimpson | |
| 5,575,280 A * | 11/1996 | Gupte et al. | 128/203.15 |
| 5,617,845 A | 4/1997 | Poss et al. | 128/203.15 |
| 5,622,166 A | 4/1997 | Eisele et al. | |
| 5,653,227 A | 8/1997 | Barnes et al. | |
| 5,657,748 A * | 8/1997 | Braithwaite | 128/203.15 |
| 5,657,794 A | 8/1997 | Briner et al. | |
| 5,664,557 A | 9/1997 | Makiej, Jr. | |
| 5,664,697 A | 9/1997 | Lambelet, Jr. et al. | |
| 5,676,130 A | 10/1997 | Gupte et al. | |
| 5,678,538 A * | 10/1997 | Drought | 128/203.15 |
| D389,570 S | 1/1998 | Savolainen | |
| 5,740,792 A | 4/1998 | Ashley et al. | |
| 5,740,794 A | 4/1998 | Smith et al. | |
| 5,775,536 A | 7/1998 | Lambelet, Jr. et al. | |
| 5,778,873 A | 7/1998 | Braithwaite | |
| 5,785,049 A | 7/1998 | Smith et al. | |
| 5,799,821 A | 9/1998 | Lambelet, Jr. et al. | |
| 5,857,457 A | 1/1999 | Hyppölä | |
| 5,875,776 A * | 3/1999 | Vaghefi | 128/203.15 |
| 5,881,719 A | 3/1999 | Gottenauer et al. | |
| 5,896,855 A | 4/1999 | Hobbs et al. | |
| 5,904,139 A | 5/1999 | Hauser | |
| 5,921,237 A | 7/1999 | Eisele et al. | |
| 5,924,417 A | 7/1999 | Braithwaite | |
| 5,941,241 A | 8/1999 | Weinstein et al. | |
| 5,944,660 A | 8/1999 | Kimball et al. | |
| 5,955,439 A | 9/1999 | Green | |
| 5,981,549 A | 11/1999 | Viner | |
| 5,996,577 A * | 12/1999 | Ohki et al. | 128/203.15 |
| 6,006,747 A | 12/1999 | Eisele et al. | |
| 6,035,463 A | 3/2000 | Pawelzik et al. | |
| 6,065,471 A * | 5/2000 | Schaeffer et al. | 128/203.15 |
| 6,065,472 A | 5/2000 | Anderson et al. | |
| 6,089,227 A | 7/2000 | Nilsson | |
| 6,116,238 A | 9/2000 | Jackson et al. | |
| 6,116,239 A * | 9/2000 | Volgyesi | 128/203.15 |
| 6,119,688 A * | 9/2000 | Whaley et al. | 128/203.15 |
| 6,125,844 A | 10/2000 | Samiotes | |
| 6,158,675 A | 12/2000 | Ogi | |
| 6,196,218 B1 | 3/2001 | Voges | |
| 6,220,243 B1 * | 4/2001 | Schaeffer et al. | 128/203.15 |
| 6,234,167 B1 | 5/2001 | Cox et al. | |
| 6,240,918 B1 | 6/2001 | Ambrosio et al. | |
| 6,254,854 B1 | 7/2001 | Edwards et al. | |
| 6,273,085 B1 | 8/2001 | Eisele et al. | |
| 6,321,747 B1 * | 11/2001 | Dmitrovic et al. | 128/203.15 |
| 6,324,428 B1 | 11/2001 | Weinberg et al. | |
| 6,325,241 B1 | 12/2001 | Garde et al. | |
| 6,328,034 B1 | 12/2001 | Eisele et al. | |
| 6,347,629 B1 | 2/2002 | Braithwaite | |
| 6,418,926 B1 * | 7/2002 | Chawla | 128/203.12 |
| 6,443,146 B1 | 9/2002 | Voges | |
| 6,484,718 B1 * | 11/2002 | Schaeffer et al. | 128/203.15 |
| 6,523,536 B2 | 2/2003 | Fugelsang et al. | |
| 6,543,443 B1 | 4/2003 | Klimowicz et al. | |
| 6,553,987 B1 * | 4/2003 | Davies | 128/200.14 |
| 6,557,550 B1 * | 5/2003 | Clarke | 128/203.15 |
| 6,557,552 B1 | 5/2003 | Cox et al. | |
| 6,601,729 B1 | 8/2003 | Papp | |
| 6,675,839 B1 | 1/2004 | Braithwaite | |
| 6,698,425 B1 | 3/2004 | Widerström | |
| 6,810,873 B1 | 11/2004 | Haikarainen et al. | |
| 6,810,874 B1 * | 11/2004 | Koskela et al. | 128/203.15 |
| 6,845,772 B2 | 1/2005 | Braithwaite et al. | |
| 6,926,003 B2 | 8/2005 | Seppälä | |
| 2003/0075172 A1 | 4/2003 | Johnson et al. | |
| 2003/0116157 A1 | 6/2003 | Braithwaite et al. | |
| 2003/0136406 A1 | 7/2003 | Seppala | |
| 2004/0011357 A1 | 1/2004 | Braithwaite | |
| 2004/0101482 A1 | 5/2004 | Sanders | |
| 2004/0236282 A1 | 11/2004 | Braithwaite | |
| 2004/0251318 A1 | 12/2004 | Braithwaite | |
| 2005/0121023 A1 | 6/2005 | Braithwaite | |

FOREIGN PATENT DOCUMENTS

| | | |
|---|---|---|
| DE | 23 46 730 A | 4/1975 |
| DE | 32 43 731 A | 5/1984 |
| DE | 195 30 240 A1 | 2/1997 |
| DE | 197 57 207 A1 | 6/1999 |
| EP | 0 045 522 A2 | 2/1982 |
| EP | 0 079 478 A1 | 5/1983 |
| EP | 0 166 294 B1 | 10/1989 |
| EP | 0 469 814 A1 | 2/1992 |
| EP | 0 514 085 B1 | 11/1992 |
| EP | 0 520 440 A1 | 12/1992 |
| EP | 0 372 777 B1 | 1/1993 |
| EP | 0 539 469 | 5/1993 |
| EP | 0 424 790 B1 | 8/1993 |
| EP | 0 626 689 B1 | 11/1994 |
| EP | 0 548 605 B1 | 1/1995 |
| EP | 0 448 204 B1 | 4/1995 |
| EP | 0 659 432 A1 | 6/1995 |

| | | |
|---|---|---|
| EP | 0 663 815 B1 | 7/1995 |
| FR | 2 516 387 A | 5/1983 |
| FR | 2 584 604 A | 1/1987 |
| FR | 2 662 936 A | 12/1991 |
| FR | 2 753 791 | 3/1998 |
| GB | 3908 | 3/1911 |
| GB | 1 242 211 | 8/1971 |
| GB | 1 573 551 | 8/1980 |
| GB | 2 041 763 A | 9/1980 |
| GB | 2 165 159 A | 4/1986 |
| GB | 2 178 965 A | 2/1987 |
| GB | 2 235 753 | 3/1991 |
| GB | 2 248 400 A | 4/1992 |
| WO | WO 90/07351 | 7/1990 |
| WO | WO 91/04011 | 4/1991 |
| WO | WO 91/11173 | 8/1991 |
| WO | WO 91/11495 | 8/1991 |
| WO | WO 91/14422 | 10/1991 |
| WO | WO 92/00771 | 1/1992 |
| WO | WO 92/03175 | 3/1992 |
| WO | WO 92/04928 | 4/1992 |
| WO | WO 92/09322 | 6/1992 |
| WO | WO 92/18188 | 10/1992 |
| WO | WO 93/00951 | 1/1993 |
| WO | WO 93/11746 | 6/1993 |

| | | | | |
|---|---|---|---|---|
| WO | WO 93/16748 | | 9/1993 | |
| WO | WO 95/00128 | | 1/1995 | |
| WO | WO 95/1577 | | 6/1995 | |
| WO | WO 97/00399 | | 1/1997 | |
| WO | WO 98/26828 | * | 6/1998 | ............ 128/203.15 |
| WO | WO98/30262 | * | 7/1998 | ............ 128/203.15 |
| WO | WO 98/31352 | | 7/1998 | |
| WO | WO 99/12597 | | 3/1999 | |
| WO | WO 99/13930 | | 3/1999 | |
| WO | WO 99/26676 | | 6/1999 | |
| WO | WO 00/12163 | | 3/2000 | |
| WO | WO 00/45878 | | 8/2000 | |
| WO | WO 00/64519 | | 11/2000 | |
| WO | WO 01/17595 A1 | | 3/2001 | |
| WO | WO 01/51030 A1 | | 7/2001 | |
| WO | WO 01/60341 A1 | | 8/2001 | |
| WO | WO 01/87378 A2 | | 11/2001 | |

OTHER PUBLICATIONS

Gerrity, T.R., "Pathophysiological and Disease Constraints on Aerosol Delivery," Chapter 1, *Respiratory Drug Delivery I*, ed. Byron, P.R., CRC Press, pp. 1-38 (1990).

* cited by examiner

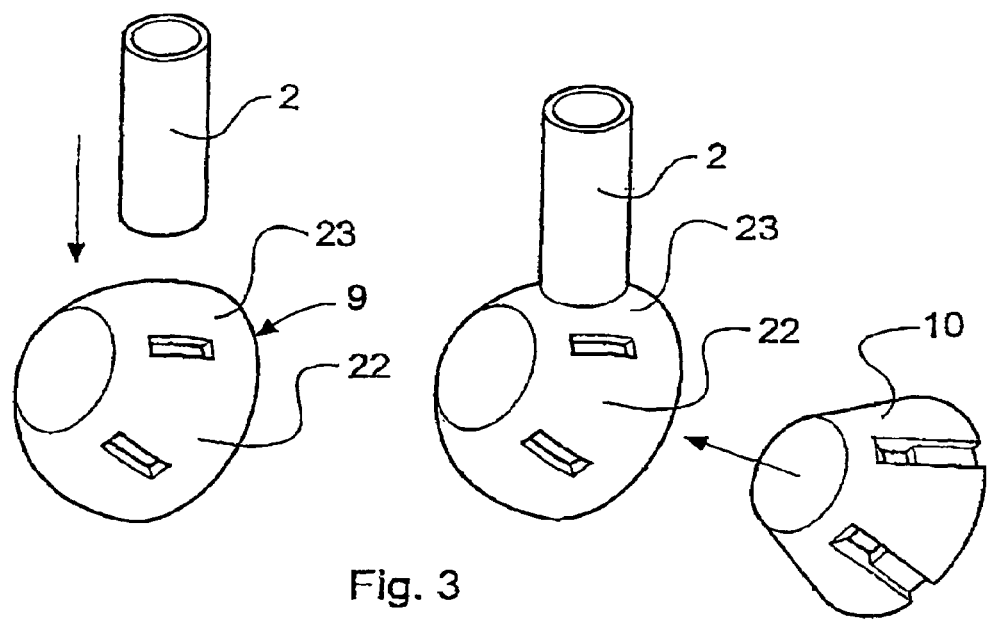
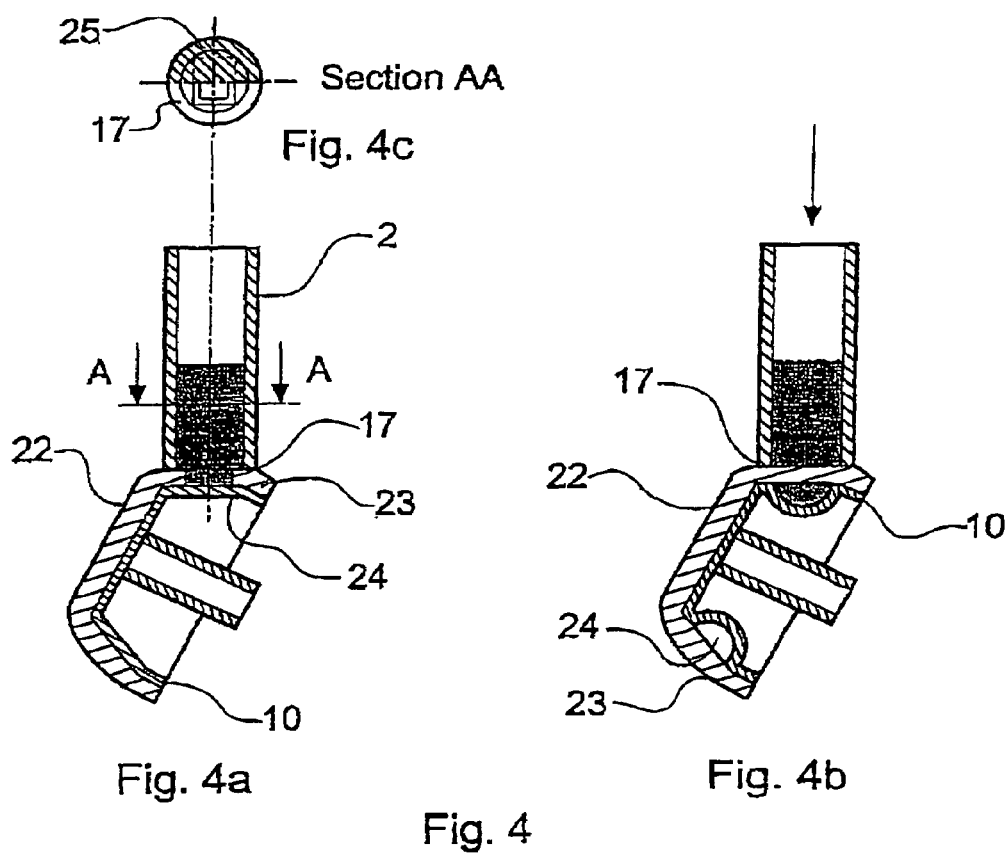

DELIVERY SYSTEM

This application is a U.S. patent application filed under 35 U.S.C. 371, based on PCT International Application No. PCT/GB00/02017, filed Jun. 5, 2000, which claims priority to Great Britain Patent Application Nos. 9913047.8 and 9916283.6, filed Jun. 5, 1999 and Jul. 13, 1999, respectively, both of which are hereby incorporated by reference in their entirety.

FIELD OF THE INVENTION

This invention relates to a novel form of medicament delivery system and to novel methods of treatment.

In particular the invention provides a medicament delivery device, such as an inhaler, which is adapted to be moisture resistant and/or provides improved air flow through the device.

BACKGROUND OF THE INVENTION

It is well established that delivery devices adapted for the delivery of dry powder medicaments suffer from the problem of contact with moisture. Such problems are particularly when hygroscopic medicaments are used or when climatic conditions give rise to high humidity. Medicament inhalers are known to suffer from such and moisture contamination of dry powder inhalers has long been held to be undesirable since the dry powder medicament may become clogged, creating problems in delivering correct dosages of medicament. Furthermore, some inhaled medicaments are themselves inherently moisture sensitive. Therefore, there has long been a desire to provide a dry powder inhaler that is resistant to moisture, that is, one that protects a medicament reservoir from moisture contamination either from the environment or from exhalation by a patient using the device and various attempts have been made to mitigate the problem.

Most attempts which have been made aim to reduce the moisture which comes into contact with a medicament, such attempts generally comprise the use of an additional chamber containing a desiccant.

International Patent Application No WO 98/41261 describes an inhalation device which includes a chamber for containing a desiccant, e.g. silica gel. Whilst the use of a desiccant gel does remove some moisture, the system is disadvantageous in that, inter alia, the leak paths are too great for the available desiccant to cope with and therefore the desiccant is only effective for a few hours, whereas there is a need for moisture resistance if at least a few months.

Similarly, International Patent Application No WO 96/08284 describes an inhaler system provided with a reservoir wherein the closed end of the reservoir is also provided with a desiccant cartridge.

International Patent Application No WO 95/32752 also describes a medicament chamber included in an inhalation apparatus and provided with a container containing a desiccant.

European Patent Application No. EP0520 440, Ambrosio et al, describes a dry powder inhaler which includes a moisture resistant barrier in the form of a flap which is designed to prevent exhaled air from a patient contaminating the medicament held in the reservoir.

SUMMARY OF THE INVENTION

U.S. Pat. No. 3,854,626, Krechmar et al, describes a pill dispensing system which comprises a moveable mechanism which prevents the ingress of moisture whilst permitting the dispensing of one or more pills.

We have now developed a medicament delivery device, e.g. a dry powder inhaler, which is able to provide a moisture proof barrier without the necessity of a desiccant.

Therefore, according to the invention we provide a medicament delivery device which comprises a medicament reservoir, a medicament delivery passage and a metering member adapted to transfer a measured dose of medicament from the medicament reservoir to the delivery passage characterised in that the device is provided with a moisture proof barrier.

The moisture proof barrier is preferentially a physical barrier as opposed to a chemical barrier, e.g. a desiccant, although it is within the scope of the present invention that a desiccant may be included in addition to the moisture proof barrier if desirable.

In a preferred embodiment the moisture proof barrier is positioned so as to prevent the ingress of moisture into the medicament reservoir, so that moisture is prevented from coming into contact with the medicament. In an especially preferred embodiment of the delivery device of the invention, the moisture proof barrier is a moisture proof sealing means.

In a preferred embodiment, the sealing means of the delivery device will operate by the delivery device being adapted to move from an inoperable position, in which the medicament reservoir is sealed, to an operative position, in which the seal is reversibly broken so that measurement and/or delivery of a dose of medicament may take place. The sealing means will generally comprise a resilient sealing member positioned at the end of the reservoir adjacent the metering member. Furthermore, the metering member is preferentially biased towards the resilient sealing member to improve the seal provided. Preferably the resilient sealing member is in a fixed position whilst the metering member moves from an inoperable to an operable position and thus from a sealing to a non-sealing position.

The resilient sealing member preferably comprises a cover adapted to fit the base of the medicament reservoir, the sealing member being provided with an aperture to permit transmission of the medicament. The resilient sealing member may comprise any conventionally known material, for example a natural or synthetic rubber, a silicon or a PTFE material, although other similar materials can be contemplated within the scope of this invention.

The moisture proof barrier of the invention may be applied to any conventionally known medicament delivery system. However, in a preferred embodiment, the medicament delivery device is an inhaler. Whilst the moisture proof barrier may be applied to any conventionally known inhaler, it is an especially preferred aspect of the invention for the inhaler to be a dry powder inhaler (DPI). DPI's are known which operate with predetermined doses of medicament, for example, the medicament may be coned in a gelatin capsule which is ruptured to release the medicament. However, a preferred inhaler of the invention is a DPI which comprises a medicament reservoir a metering member which is adapted to measure a selected amount of medicament for inhalation. Thus, in an especially preferred embodiment the metering member is rotatable from an operable to an inoperable position. The metering member may comprise a dispensing member and a moisture resistant member, e.g. a moisture resistant sleeve. In such an embodiment the moisture resistant member is provided with one or more measure chambers adapted to measure a predetermined dosage of medicament. Thus, in the operable position, the position of measuring chamber of the metering member corresponds with the aperture in the resilient sealing member so that medicament enters the measuring chamber. The moisture resistant member may then be rotated so that the reservoir is sealed again by the wall of the moisture resistant member. At the same time the medicament is transferred from the measuring chamber of the moisture resistant sleeve to the dispensing chamber of the dispensing member.

An example of a preferred DPI is CLICKHALER, produced by Innovata Biomed in the UK. Such a device is described in European Patent No 0 539 469. Thus, the metering member may be a frusto conical member such as described in European Patent No 0 539 469.

Therefore, the metering member may comprise a frusto conical dispensing member with a corresponding moisture resistant sleeve, such that the sleeve overlies the dispensing member. Thus, the measuring chamber may comprise outer side walls which are provided by an aperture in the wall of the moisture resistant sleeve and the base of the measuring chamber may be provided by the frusto conical wall of the dispensing member. Preferably the moisture resistant sleeve is provided with a plurality of apertures and thereby a plurality of measuring chambers.

The use of the frusto-conical shape in the wall of the metering member containing the measuring chamber allows a good seal to be obtained between the metering member and a seat against which the frusto-conical wall mates.

Therefore, the frusto conical metering member may itself comprise a combination of a frusto conical dispensing member and a frusto conical moisture resist sleeve which forms a snug fit over the dispensing member. The moisture resistant sleeve may itself be moveable eg rotatable, from a sealing to a non-sealing position as herein before described and vice verse. Such a moisture resistant sleeve may comprise any conventionally known material but is preferentially a plastics material, e.g. the same material as the metering member.

The dispensing member and the moisture resistant sleeve can, preferentially, be adapted so as to act together as a medicament measuring/dispensing member. The preferred metering member comprises a dispensing member provided with one or more dispensing cups and a moisture resistant sleeve provided with one or more apertures. Preferably the dispensing member comprises a plurality of dispensing cups and the sleeve comprises a plurality of apertures. It is especially preferred that the dispensing member comprises an equivalent number of dispensing cups to apertures in the sleeve.

We have especially found that if the moisture resistant sleeve comprises a frusto hemispherical cone, then an improved seal is achieved between the medicament reservoir and the sleeve. When a frusto hemispherical cone sleeve is used, the arcuate base of the reservoir is able to make more uniform contact with the curved surface of the cone and therefore an improved seal is achieved. Thus, it is especially preferred that the outer walls of the cone which are hemispherical. Furthermore, the inner walls of the cone are preferably contoured to form a good mate with the frusto conical dispensing member.

Thus, in operation, the metering member may be moved to a first position in which the medicament is transferred to a first measuring chamber in the moisture resistant sleeve, the device is then moved to a second position in which medicament is transferred from the measuring chamber to a dispensing cup in the dispensing member and then to a third position where medicament is delivered to the delivery passage.

The dispensing member may be a conventionally known member such as a frusto conical member described herein and in EP 0 539 469. However, we have also found the use of a moisture resistant sleeve permits a dispensing chamber to be provided with an air inlet, e.g. an air duct. Previously, the use of an air inlet was felt to be undesirable since it might effect the accuracy of the measurement of the medicament dose. However, by use of a system wherein the medicament is first transferred to a measuring chamber and then subsequently to a dispensing cup, the cup in the dispensing member may be provided with an air inlet without any loss in accuracy of the dosage delivered. Furthermore, improved air flow provides greater likelihood of complete emptying of the dispensing cup and thereby provide an inhaler with improved performance. Clearly, an inhaler with such improved performance is advantageous per se, regardless of whether such an inhaler is moisture resistant.

Thus according to an alternative feature of the invention we provide a dry powder inhaler which comprises a medicament reservoir, an inhalation passage for the delivery of the medicament and a metering member adapted to transfer a measured dose of medicament from the medicament reservoir to the inhalation passage characterised in that the metering member comprises a measuring member adapted to measure a pre-defined dosage of medicament and moveable from a measuring to a non-measuring position; and a dispensing member adapted to receive the measured dosage of medicament from the measuring member and to deliver the medicament to the inhalation passage, the dispensing member being moveable from a medicament receiving position to a medicament delivering position.

In the preferred embodiment the dispensing member is provided with one or more medicament dispensing cups, said cups being provided with a duct so as to provide a flow of air through the cup and into the inhalation passage upon operation of the device.

By the term dry powder we mean a medicament in finely divided form.

A variety of medicaments may be administered by using the inhaler of the invention, optionally with a conventionally known pharmaceutically acceptable adjuvant, diluent or carrier. Such medicaments are generally antibiotics, bronchodilators or other anti-asthma drugs. Such medicaments include, but are not limited to $\beta_2$-agonists, e.g. fenoterol, formoterol, pirbuterol, reproterol, rimiterol, salbutamol, salmeterol and terbutaline; non-selective beta-stimulants such as isoprenaline; xanthine bronchodilators, e.g. theophylline, aminophylline and choline theophyllinate; anticholinergics, e.g. ipratropium bromide; mast cell stabilisers, e.g. sodium cromoglycate and ketotifen; bronchial anti-inflammatory agents, e.g. nedocromil sodium; and steroids, e.g. beclomethasone dipropionate, fluticasone, budesonide and flunisolide; and combinations thereof.

Specific combinations of medicaments which may be mentioned include combinations of steroids, such as, beclomethasone dipropionate, fluticasone, budesonide and flunisolide; and combinations of to $\beta_2$-agonists, such as, formoterol and salmeterol. It is also within the scope of this invention to include combinations of one or more of the aforementioned steroids with one or more of the aforementioned $\beta_2$-agonists.

The inhaler of the invention is especially suitable for use in the treatment or alleviation of respiratory disorders. Thus according to the invention we also provide a method of administering a dry powder inhalation medicament using an inhaler as hereinbefore described.

We further provide a method of treatment of a patient with a respiratory disorder which comprises the administration of a combination of medicaments using an inhaler as hereinbefore described.

BRIEF DESCRIPTION OF THE DRAWINGS

The invention will now be described by way of example only and with reference to the accompanying drawings in which:

FIG. 3 is a perspective view of a moisture resistant sleeve comprising a frusto hemispherical cone, and FIGS. 4a–b are cross-sectional views of a moisture resistant sleeve comprising a frusto herispherical cone.

DETAILED DESCRIPTION OF THE INVENTION

Figure 1:
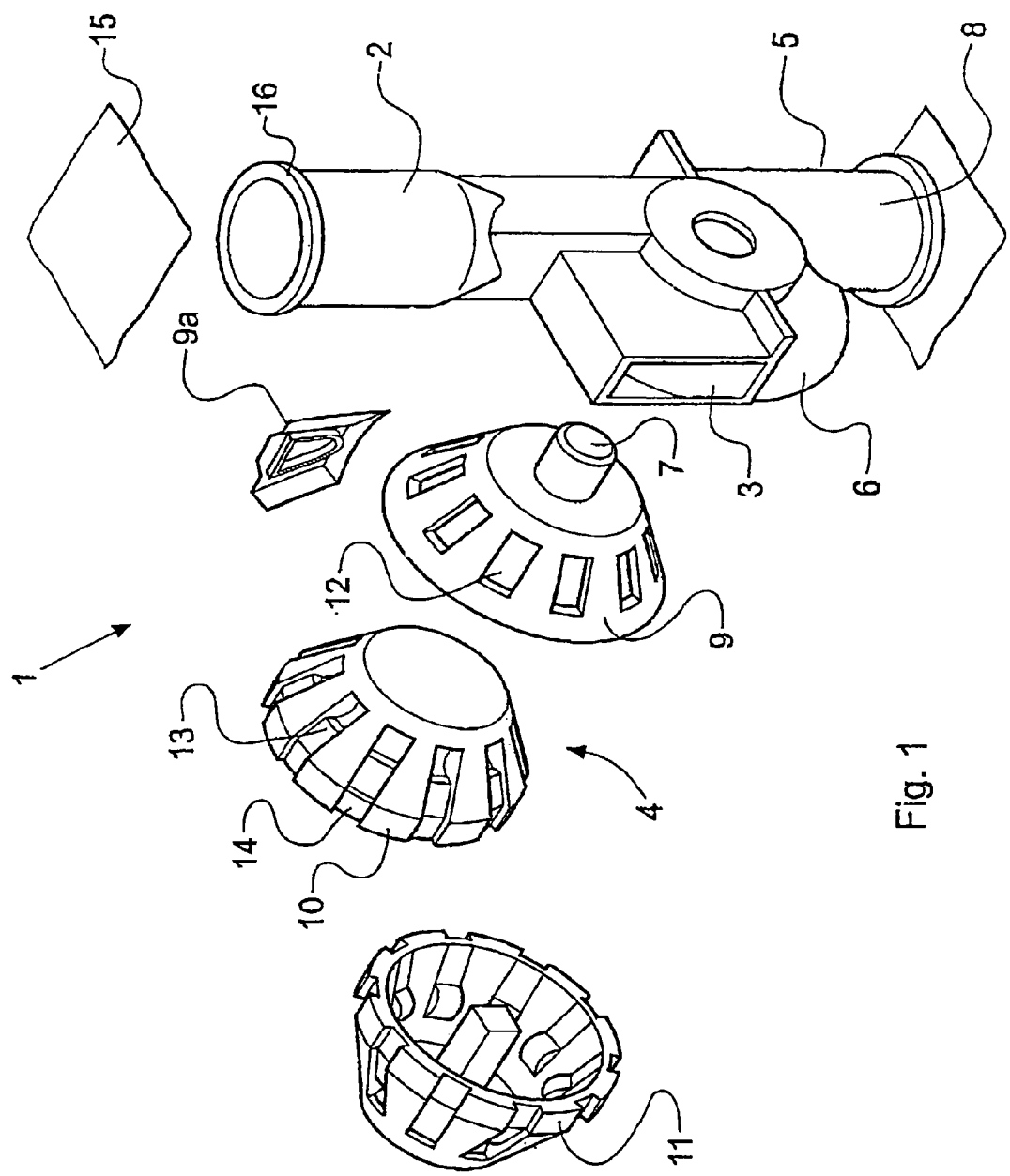
FIG. 1 is a perspective view of an inhalation device of the invention.

With reference to FIG. 1, a dry powder inhaler (1) comprises a medicament reservoir (2) comprising an essentially conical member; an inhalation passage (3) and a metering member (4). The inhalation passage (3) is connected to the medicament reservoir (2) by a reservoir support (5) ad is itself connected to recess (6) which provides a seat for the metering member (4). The metering member (4) is rotatable about an axis (7) from a medicament receiving position, to a medicament delivery position and then to an emptying position to allowing any residual medicament to be emptied into a waste box (8).

The recess (6) is essentially frusto conical in shape to enable it to provide a seal for the metering member (4). The metering member (4) comprises a frusto conical moisture resistant sleeve (9) which forms a snug fit between recess (6) and a dispensing member (10). The dispensing member (10) is also provided with a back plate (11).

The moisture resistant sleeve (9) abuts at the resilient seal (9a) to form a moisture resistant seal.

The moisture resistant sleeve (9) is also provided with a plurality of measuring chambers which comprise apertures (12) dimensioned to measure a predetermined amount of medicament and to fit over cups (13) in the dispensing member (10). In a preferred embodiment, each of the cups (13) are also provided with a duct (14). The medicament reservoir (2) is also provided with a moisture resistant, eg foil, cover (15) at it's end (16) distal from the metering member (4).

Figure 2:
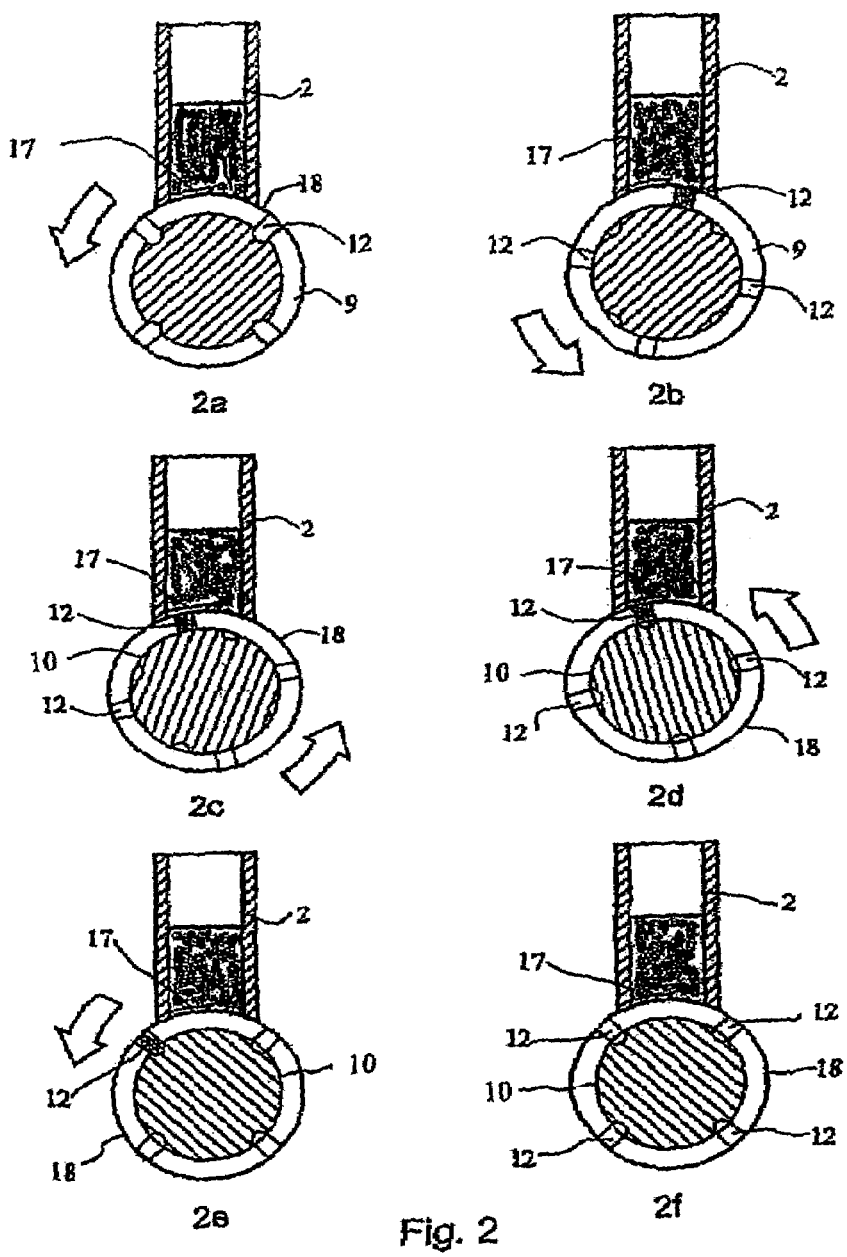
FIGS. 2a–f are schematic representations of the sealing and measuring mechanism.

With reference to FIG. 2, in which FIG. 2a the metering device is in a closed position, FIG. 2b the metering device is in a measuring position, FIG. 2c the metering device is in a seal transitory position, FIG. 2d the metering device is in a medicament transfer position, FIG. 2e the metering device is in a medicament delivery position; and FIG. 2f the metering device is returned to the closed position.

In FIG. 2a the metering device (4) is in the closed position and the medicament reservoir (2) is isolated and a seal formed between the sealing member (17) and the surface (18) of the moisture resistant sleeve (9). In FIG. 2b, the moisture resistant sleeve (9) is rotated in an anti clockwise direction so that the aperture/measuring chamber (12) corresponds with the aperture in the sealing member (17). The aperture/measuring chamber (12) forms a cup with the surface of the dispensing member (10).

In FIG. 2c the moisture resistant sleeve (9) is further rotated so that the aperture/measuring chamber (12) sits below the sealing member (17). The internal edge of the sealing member (17) scrapes any excess medicament from the aperture/measuring chamber (12) to leave a measured dose.

In FIG. 2d the dispensing member (10) is rotated in an anticlockwise direction so that the dispensing cup (13) corresponds with the aperture/measuring chamber (12) allowing medicament to transfer from the aperture/measuring chamber (12) to the dispensing cup (13).

In FIG. 2e both the dispensing member (10) and the moisture resistant sleeve (9) are rotated anticlockwise to expose them and the medicament to the inhalation passage (3). The patient can then inhale the medicament.

In FIG. 2f the inhalation device remains in the close position ready for use.

With reference to FIGS. 3 and 4, a moisture resistant sleeve (9) comprises a frusto hemispherical cone (22) wherein the outer surface (23) is arcuate. The inner surface (24) acts as a female member to form a snug fit with the frusto conical dispensing member (10). Downward pressure in the medicament reservoir (2) ensures a constant moisture tight seal between the sealing member (17) and the frusto hemispherical cone (22). Furthermore, referring to FIG. 4c, the leading edge (25) of the sealing member (17) is capable of acting as a scraper or a cleaning edge, removing any excess medicament from the measuring chamber upon rotation of the metering member.

A variety of mechanisms may be used for the operation of the inhaler. One preferred mechanism is for movement from the closed to the measuring position to be achieved by removal of a month piece which is operably linked to the moisture resistor. Movement from the measuring position to the transitory position would use a mechanism similar to that described in EP 0 539 469, e.g. by depressing the button half way. Movement to the transfer position being achieved by further depressing the button, and then depression completely, moving the metering cone and the moisture resistor to the delivery position.

The invention claimed is:

1. A medicament delivery device comprising:
   a medicament reservoir;
   an inhalation passage; and
   a metering member, provided with at least one dispensing cup, adapted to transfer a measured dose of medicament from the medicament reservoir to a medicament delivery position;
   wherein the metering member comprises a medicament dispensing member and a medicament measuring member associated therewith, said medicament measuring member being provided with at least one measuring chamber for transferring medicament from the reservoir to the dispensing cup,
   the arrangement being such that the metering member can be moved from a measuring position, in which medicament is transferred from the reservoir to the measuring chamber, to a medicament transfer position, in which medicament is transferred from the measuring chamber to the dispensing cup, and to a medicament delivery position and wherein the dispensing cup is provided with an air duct.

2. A medicament delivery device according to claim 1, characterized in that the device is provided with a moisture proof barrier.

3. The delivery device according to claim 1 or 2 wherein said metering member comprises a moisture resistant sleeve.

4. The delivery device according to claim 3 wherein at least one aperture in said sleeve provides said at least one measuring chamber.

5. An inhaler comprising:
- a medicament reservoir;
- an inhalation passage; and
- a metering member, provided with at least one dispensing cup, adapted to transfer a measured dose of medicament from the medicament reservoir to a medicament delivery position;

wherein the metering member comprises a medicament dispensing member and a medicament measuring member associated therewith, said medicament measuring member being provided with at least one measuring chamber for transferring medicament from the reservoir to said dispensing cup, the arrangement being such that the metering member can be moved from a measuring position, in which medicament is transferred from the reservoir to the measuring chamber, to a medicament transfer position, in which medicament is transferred from the measuring chamber to the dispensing cup, and to a medicament delivery position; and wherein the dispensing cup is provided with a duct to provide a flow of air through the cup and into the inhalation passage upon operation of the inhaler.

6. An inhaler according to claim 5 characterized in that the metering member comprises an outer sleeve and a dispensing member.

* * * * *